(12) United States Patent
Hirsh et al.

(10) Patent No.: US 6,582,737 B2
(45) Date of Patent: *Jun. 24, 2003

(54) PHARMACEUTICAL COMPOSITION CONTAINING TWO ACTIVE INGREDIENTS FOR SMOKING CESSATION

(75) Inventors: Mark Hirsh, Wellesley, MA (US); Kamal K. Midha, Hamilton HM (BM); Hans E. Junginger, Wellesley, MA (US)

(73) Assignee: Peirce Management, LLC, Wellesley, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/962,927

(22) Filed: Sep. 25, 2001

(65) Prior Publication Data

US 2003/0064092 A1 Apr. 3, 2003

(51) Int. Cl.⁷ .............................................. A61K 35/78
(52) U.S. Cl. ..................... 424/751; 424/449; 424/451; 424/440; 424/464; 514/343
(58) Field of Search ................................ 424/449, 451, 424/440, 464, 751; 514/343

(56) References Cited

U.S. PATENT DOCUMENTS

| 5,837,280 A | 11/1998 | Kenealy |
| 5,972,974 A | 10/1999 | Keenan |
| 6,004,970 A | 12/1999 | O'Malley |
| 6,280,763 B1 * | 8/2001 | Midha et al. |
| 6,312,716 B1 * | 11/2001 | Midha et al. |

* cited by examiner

Primary Examiner—Leon B. Lankford, Jr.
Assistant Examiner—Susan D. Coe
(74) Attorney, Agent, or Firm—Herbert Dubno; Jonathan Myers

(57) ABSTRACT

A kit to alleviate tobacco-smoking withdrawal symptoms in a patient is disclosed which comprises:

(a) a therapeutically effective amount of nicotine, at least one active nicotine metabolite, a combination of nicotine and an active nicotine metabolite, or an azapirone, or a pharmaceutically acceptable salt thereof;

(b) a transdermal delivery system consisting essentially of a bupropion base in a therapeutically effective amount; and (c) a packaging material surrounding (a) and (b).

22 Claims, 2 Drawing Sheets

PHARMACEUTICAL COMPOSITION CONTAINING TWO ACTIVE INGREDIENTS FOR SMOKING CESSATION

CROSS REFERENCE TO RELATED APPLICATIONS

This application is related to our copending U.S. patent applications Ser. No. 09/309,075 filed May 10, 1999, now U.S. Pat. No. 6,280,763, and Ser. No. 09/562,178 filed May 2, 2000, the entire contents of which are both expressly incorporated herein by reference.

FIELD OF THE INVENTION

The invention relates to pharmaceutical compositions to alleviate tobacco withdrawal syndrome. The invention further relates to a therapeutic method of alleviating tobacco withdrawal syndrome and craving associated with cessation of nicotine use in a patient who is refraining from smoking tobacco by administration of the pharmaceutical compositions. The pharmaceutical compositions and methods of alleviating tobacco withdrawal syndrome effectively alleviate the symptoms of depression which is related to the withdrawal of nicotine.

BACKGROUND OF THE INVENTION

Despite the potential adverse health effects associated with smoking, the vast majority of cigarette smokers are unable to cease smoking. The lack of success may be related to the tobacco withdrawal syndrome that most smokers experience when they attempt to cease smoking. The lack of success may be related to the tobacco withdrawal syndrome that most smokers experience when they attempt to cease smoking. Smoking withdrawal symptoms are associated with craving for cigarettes; the craving is the most difficult symptom to alleviate.

There has been a large body of research focused on the factors that precipitate craving in an attempt to understand these aspects better to be able to deal with these severe issues. It is also believed by some investigators that smokers can be divided into two categories: cravers and non-cravers. These separate populations have different responses to smoking cessation therapy. Most commercial replacement products available for nicotine smoking cessation have been lacking in dealing with the issue of satisfying craving for nicotine cigarette smoking. The most common effects are similar to those in almost all abstinence syndromes and include decreased heart rate, anxiety, tension, difficulty concentrating, impatience, depression, increased appetite with accompanying weight gain, inability and restlessness. Most withdrawal effects occur within 24 hours and peak in the first 1 to 2 weeks and significantly decrease after one month. It is widely believed that the effects of abstinence from tobacco are due to nicotine deprivation, and that abstinence from smoking prevents smokers from stopping the habit of smoking.

Of the pharmacological approaches to aiding tobacco use cessation, nicotine gum or nicotine patches are the most widely used. Nicotine gum and transdermal patches decrease abstinence discomfort. The nicotine nasal spray inhaler is also beneficial in decreasing abstinence discomfort. Bupropion has been proven to reduce agitation, anxiety, and insomnia; additionally, there are studies which indicate that bupropion will also assist in weight maintenance.

Nicotine acts as an agonist at the nicotine cholinergic receptors at the autonomic ganglia in the adrenal medulla, at neuromuscular junctions, and in the brain. Nicotine's positive reinforcing properties are believed to be the result of the release of neurotransmitter including acetylcholine, beta-endorphin, dopamine, norepinephrine, serotonin, and other compounds that mediate pleasure, arousal, elevated mood, appetite, and other desirable psychological states.

When nicotine gum is chewed, nicotine is displaced from polarities by alkaline salts. Buffering a gum to a pH of 8.5 enhances the absorption of nicotine; the rate of absorption of the oral route is slower than that from the lungs during smoking. The time to peak concentration of the nicotine gum is from 15 to 30 minutes after the start of chewing.

Bupropion acts as an antidepressant. Although the exact mechanism of the antidepressant action is unclear, it is thought to be mediated by bupropion's noradrenergic and/or dopaminenergic effects. Bupropion is a weak inhibitor of neuronal uptake of norepinephrine, serotonin, and dopamine, although inhibition of uptake occurs at higher doses than those required for bupropion's antidepressant effects.

U.S. Pat. No. 5,837,280 discloses compositions and methods for the transdermal administration of azapirones for treating a variety of treating psychogenic symptomatology, including the symptoms associated with nicotine dependence and the symptoms associated with withdrawal from tobacco. There is no mention of administration of the azapirones by any route in conjunction with transdermal administration of bupropion base.

U.S. Pat. No. 5,972,974 discloses compositions contained in a patch for transdermal administration where the transdermal patch contains nicotine or an active nicotine metabolite. The nicotine or active nicotine metabolite is transdermally administered to patients including patients who are undergoing the effects of abstinence from tobacco. There is no suggestion in this reference to administer nicotine or an active nicotine metabolite in conjunction with transdermal administration of bupropion base to alleviate tobacco-smoking withdrawal symptoms.

U.S. Pat. No. 6,004,970 discloses a method of treating a patient for nicotine dependency by administering to the patient an effective amount of naltrexone and an effective amount of nicotine. The nicotine may be administered to the patient using a nicotine patch and the naltrexone may be administered intradermally. An antidepressant such as WELBUTRIN$^R$ which is bupropion hydrochloride may be administered to the patient in conjunction with the nicotine and the naltrexone. Intradermal administration is mentioned as one route of administration.

It is noted that the present invention is directed to the administration of nicotine or an active nicotine metabolite in conjunction with a bupropion base the latter administered transdermally through a patch and not in conjunction with a bupropion salt such as bupropion hydrochloride. Furthermore an opioid antagonist such as naltrexone is not a part of the present invention and thus the present invention is very different from the invention disclosed in U.S. Pat. No. 6,004,970.

Hydroxybupropion, an effective metabolite of bupropion, may have clinically significant antidepressant effects.

OBJECTS OF THE INVENTION

It is an object of the invention to provide a pharmaceutical composition to assist a smoker to gradually give up the need to smoke tobacco and the need for nicotine.

It is a further object of the invention to provide relief to the patient of symptoms associated with withdrawal of smoking cigarettes, including agitation and depression.

SUMMARY OF THE INVENTION

Quitting smoking is hard. Smoking is a physical addiction as well as a habituation. The pharmaceutical composition according to the present invention is a treatment package that has been designed to assist in slowly weaning the patient, off of nicotine, while eliminating the depressive state associated with withdrawal from smoking. Because smoking is such a strong habit it is necessary to provide a well-contained therapy. The unit will assist the patient by allowing him/her to eliminate the habit of smoking over time as well as to provide relief of symptoms associated with withdrawal of smoking cigarettes.

The present invention is directed to a pharmaceutical composition in unit dosage form combining two pharmaceutically active ingredients to alleviate tobacco-smoking withdrawal symptoms which comprises:

(a) a therapeutically effective amount of nicotine, at least one active nicotine metabolite, a combination of nicotine and an active nicotine metabolite, or an azapirone, or a pharmaceutically acceptable salt thereof; and (b) a transdermal delivery system consisting essentially of a bupropion base in a therapeutically effective amount.

Preferably the transdermal delivery system is a patch for transdermal delivery of bupropion to a mammalian subject, said patch comprising:

(i) a flexible, inert backing layer incapable of absorbing bupropion base;

(ii) a release liner through which bupropion base is not permeable; and (iii) a reservoir located between the backing layer and the release liner, said reservoir having a bupropion-transfer surface adjacent to the release liner and adapted to contact the skin of the patient and sufficient to transfer an effective dosage of bupropion base through the skin of said patient into the bloodstream of said patient, which comprises:

(1) a therapeutically effective amount of bupropion base selected from the group which consists of (+)-bupropion base, (−)-bupropion base and racemic bupropion base and mixtures thereof; and (2) means for securing the bupropion-transfer surface area of said reservoir to the skin of the patient.

The bupropion base contained in the reservoir in the transdermal patch may be stabilized with a stabilizer. Such stabilizers for stabilization of the bupropion base preferably include L-ascorbic acid palmitate, tocopherol solution in alcohol, butylated hydroxyanisole, vitamin E succinate, Vitamin E 700 acetate, or L-ascorbic acid G palmitate. Preferably the stabilizer is present in the reservoir containing the bupropion base in an amount of 2.7 to 27% by weight of the bupropion base.

Preparation of the transdermal delivery system containing the bupropion base and the transdermal patch containing the stabilized bupropion base may be found respectively in our copending U.S. patent applications Ser. No. 09/309,075 filed May 10, 1999 and Ser. No. 09/562,178 filed May 2, 2000, the entire contents of which are both expressly incorporated herein by reference.

The unit dosage form containing nicotine or the combination of nicotine and its active metabolite, the azapirone or a pharmaceutically acceptable salt thereof may be in an oral or intraoral dose as a tablet or capsule, may be in an oral dosage form dissolved in an aqueous solution, may be contained in a patch for transdermal delivery including location within the reservoir containing the bupropion base in the transdermal patch as well as location within a transdermal patch separate from the transdermal patch containing the bupropion base, may be in a nasal spray inhaler or nasal vapor inhaler for intranasal administration, and may be in the form of a lozenge or a chewing gum suitable for intraoral administration. Such transdermal patches containing the azapirone may be found for example in U.S. Pat. No. 5,837,280.

Preferred active nicotine metabolites include cotinine, nornicotine, norcotinine, nicotine N-oxide, cotinine N-oxide, 3-hydroxy-cotinine, 5-hydroxy-cotinine or a pharmaceutically acceptable salt thereof.

The azapirone is preferably buspirone, but may also include gepirone, ipsapirone, tandospirone, WY-47,846, MDL-73005 EF or BP-554.

The invention also includes a method of alleviating tobacco-smoking withdrawal symptoms in a patient who is refraining from smoking tobacco which comprises the step of administering to said patient a therapeutically effective amount of a pharmaceutical composition in unit dosage form combining two pharmaceutically active ingredients to alleviate tobacco-smoking withdrawal symptoms which comprises:

(a) a therapeutically effective amount of nicotine, at least one active nicotine metabolite, a combination of nicotine and an active nicotine metabolite, or an azapirone, or a pharmaceutically acceptable salt thereof; and (b) a transdermal delivery system consisting essentially of a bupropion base in a therapeutically effective amount.

Preferably the transdermal delivery system is a patch for transdermal delivery of bupropion to a mammalian subject, said patch comprising:

(i) a flexible, inert backing layer incapable of absorbing bupropion base;

(ii) a release liner through which bupropion base is not permeable; and (iii) a reservoir located between the backing layer and the release liner, said reservoir having a bupropion-transfer surface adjacent to the release liner and adapted to contact the skin of the patient and sufficient to transfer an effective dosage of bupropion base through the skin of said patient into the bloodstream of said patient, which comprises:

(1) a therapeutically effective amount of bupropion base selected from the group which consists of (+)-bupropion base, (−)-bupropion base and racemic bupropion base and mixtures thereof; and (2) means for securing the bupropion-transfer surface area of said reservoir to the skin of the patient.

Preferably the therapeutically effective amount of nicotine, a combination of nicotine and its active metabolite, an azapirone, or a pharmaceutically acceptable salt thereof ranges from 1 to 100 mg/kg of body weight of the patient. Preferably the therapeutically effective amount of transdermally administered bupropion base selected from the group which consists of (+)-bupropion base, (−)-bupropion base and racemic bupropion base and mixtures thereof ranges between 40 and 300 mg/day.

The present invention also provides an article of manufacture in the form of a kit comprising packaging material, such as a bottle, box, tube, sprayer, insufflator, envelope and the like, and two units containing dosage units of pharmaceutical agents contained within said packaging material, wherein said pharmaceutical agents comprise nicotine, a nicotine metabolite, or a combination of nicotine metabolites, or pharmaceutically acceptable salts thereof in an amount effective to alleviate tobacco withdrawal syndrome. The other pharmaceutical agent will consist of a transdermal patch system containing bupropion in its base form and/or the isomers of bupropion in combination with bupropion. The invention also includes the combination of the transdermal bupropion patch and nicotine, at least one of its active metabolites, a combination of nicotine and one of its active metabolites, an azapirone or their pharmaceutically acceptable salts.

Preparation of the Transdermal Patch Containing Bupropion Base

In one embodiment, the transdermal system contains bupropion base either as the racemate or as the (+) isomer or as the (−) isomer in acrylic-based polymer pressure sensitive adhesives with a resinous cross-linking agent (either based on silicone polymers or polyacrylates and alcohol) to provide a continuous source of active ingredients. Each unit is sealed in a paper polyethylene-foil pouch. Isomers of bupropion can be separated by known methods. Stabilizers that may optionally be included in the reservoir of the patch include Vitamin E preferably as DL Tocopheral solution in alcohol, Vitamin E succinate or Vitamin E 700 acetate and butylated hydroxy anisole.

The reservoir may include a carrier or vehicle. The "Carriers" or "vehicles" refer to carrier materials suitable for transdermal drug administration and include any such materials known in the art, such as any liquid, gel solvent, liquid diluent, solubilizer, or the like, which is nontoxic and which does not interact with other components of the composition in a deleterious manner. Examples of suitable carriers for use herein include water, silicone, liquid sugars, waxes, petroleum jelly, and a variety of other materials. The term "carrier" or "vehicle" can also refer to crystallization inhibitors, or other types of additives useful for facilitating transdermal drug delivery. Suitable materials for this layer include, for example, polysiloxanes, polyisobutylenes, polyurethanes, plasticized ethylenevinyl acetate copolymers, low molecular weight polyether amide block polymers (e.g., PEBAX), tacky rubbers, such as polyisobutene, polystyrene-isoprene copolymers, polystyrene-butadiene copolymers, and mixtures thereof. Presently preferred adhesive materials for use as reservoir layer are polyisobutylenes, silicones, polyurethanes and polyacrylates, with polyisobutylenes particularly preferred. The carrier will be composed of these materials in such a way to achieve a controlled occlusion of the skin achieving optimal enhancement of drug penetration across the skin with minimal skin irritation (which may be caused by complete occlusivity of the system).

In a preferred embodiment, the reservoir matrix may include a dispersing agent which aids in maintaining the particulate phase dispersed in the continuous phase. In other embodiments, non-ionic excipients, such as lauric alcohol, propylene glycol monolaurate, myristyl lactate, lauryl lactate, or the like, facilitate dispersion.

The cold flow properties of the polymer adhesives of the bupropion delivery system are considered acceptable when adhesion of the transdermal patch to the skin of the user remains high throughout the drug delivery period and the adhesive does not extend beyond the boundary of the patch.

The release liner is a disposable element which protects the device prior to application. Typically, the release liner is formed form a material impermeable to the drug, vehicle and adhesive, and which is easily stripped from the contact adhesive. Release liners are typically treated with silicone or fluorocarbons. Silicone-coated polyester is a preferred embodiment. Another material may be silicone-coated aluminum.

The backing layer functions as the primary structural element of the device and provides the device with much of its flexibility, drape and, preferably, controlled occlusivity. The material used for the backing layer should be inert and incapable of absorbing drug, enhancer or other components of the pharmaceutical composition contained within the device. The backing is preferably made of one or more sheets or films of a flexible material that serves as a protective covering to prevent loss of drug or vehicle or both by transmission through the upper surface of the device, and imparts a desired degree of occlusivity to the device, such that the area of the skin covered on application becomes hydrated. The material used for the backing layer may permit the device to follow the contours of the skin and be worn comfortably on areas of the skin, such as at joints or other points of flexure, that are normally subjected to mechanical strain with little or no likelihood of the device disengaging from the skin due to differences in the flexibility or resiliency of the skin and the device. Examples of materials useful for the backing layer are polyesters, polyethylene, polypropylene, polyurethanes and polyether amides. The layer is preferably in the range of about 15 micrometers to about 20 micrometers in thickness.

The bupropion transdermal infusion system is a flat unit designed to provide continuous controlled release of bupropion base as racemate or its isomers through the intact skin. The rate of release of bupropion base or its isomers is linearly dependent upon the area of the applied system; each square cm of the applied system delivers approximately 2 mg to 7.5 mg/cm$^2$. In one embodiment, the patch size can range from about five to forty square centimeters. The rate of delivery of the bupropion from a forty square centimeter patch can range from about 10 mg/day to 300 mg/day for all methods of treatment.

Bupropion hydrochloride is commercially available under the name Welbutrin and Welbutrin from Burroughs Wellcome. For bupropion (1-(3-chlorophenyl-Z-[(1,1-dimethylethyl)amino]-1-propanone, its preparation is described in U.S. Pat. Nos. 3,819,706 and 3,885,046, wherein the teachings of each patent are incorporated by reference.

Preparation of bupropion base can be carried out by a suitable method. In one embodiment, 1.2 g bupropion HCl is dissolved in 20 ml of distilled water to which 0.1 N NaOH is added until the pH is about 12. Then this mixture is extracted with 50 ml of diethylether by shaking followed by centrifugation. The ether phase containing the bupropion base is separated and the remaining watery phase is treated three times with 80 ml diethylether. The unified ether phases are dried (removal of residual water) by adding 15 g anhydrous $K_2CO_3$, filtrated and the ether is evaporated at 50° C. under vacuum (rotavapor). The residual phase (bupropion base) (1.0 g) is dissolved in 6 ml propylene glycol and stored until further use under nitrogen gas in a tight bottle in the dark. Bupropion base can be prepared by other procedures that are known as state of the art.

PREPARATION EXAMPLE

Preparation of a stabilized bupropion base transdermal patch.

The following composition is contained in the reservoir:

|  | Component | % w/w on a dry basis |
|---|---|---|
| 1. | Racemic bupropion base | 18 |
| 2. | Polyisobutylene adhesive | 20 |
| 3. | Vitamin E succinate | 2 |
| 4. | Petroleum jelly | 60 |

Racemic bupropion base (18 g), Vitamin E succinate (2 g), polyisobutylene adhesive (20 g) and petroleum jelly (60 g) are mixed at ambient temperature until all of the ingredients have dissolved. Then an acrylic based polymer pressure sensitive adhesive is added to the mixture. The mixture is allowed to stand for several minutes to remove air bubbles.

The mixture was formulated into a patch system as follows:

Using an appropriate coating device (square tool steel Multi-Clearance Applicator sold by BYC Gardner) with a 5 or 10 mil (about 130 to 250 microns) casting gap, a layer of the mixture was coated onto a polyester backing layer having a thickness of about 100 microns, and dried in an oven at 76 to 78° C. for 15 to 18 minutes. A silicone-coated polyester release liner was then laminated onto the opposite side of the mixture from the backing layer.

The multi-layer system was then cut into a 5 cm square patch. The thickness of the patch is about 500 microns.

DETAILED DESCRIPTION OF THE DRAWINGS

Figure 1:
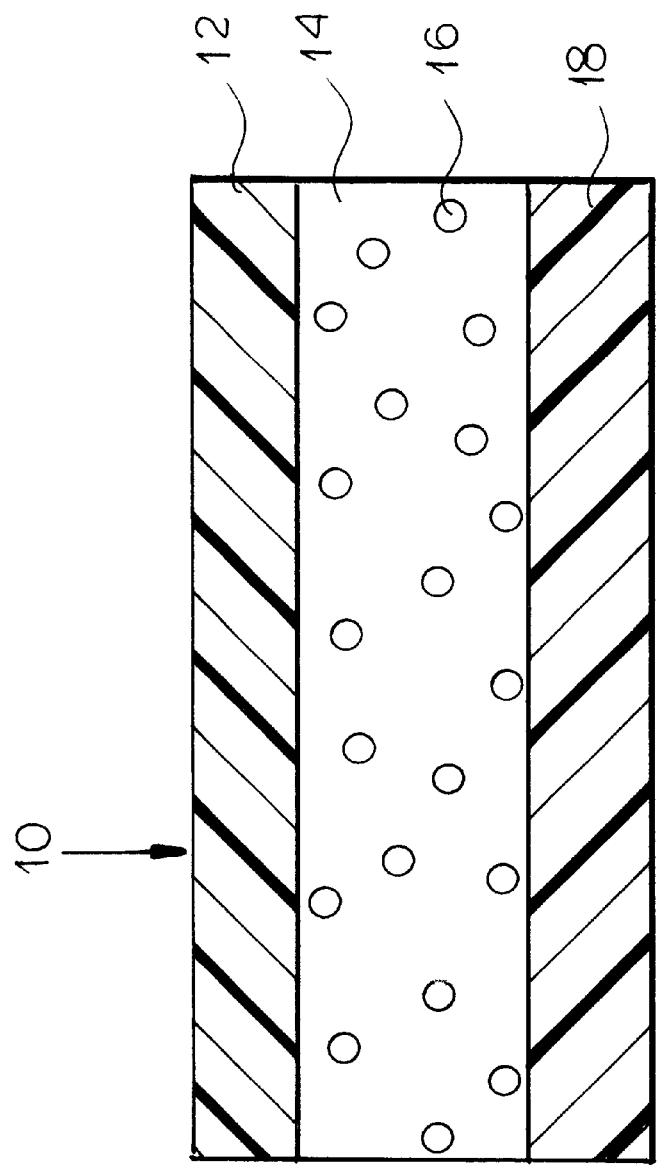
FIG. 1 is a schematic illustration of a transdermal delivery system (patch) containing bupropion base for use according to the present invention.

According to FIG. 1 patch or system 10 is in the form of a laminated composite having a backing layer 12, a reservoir layer 14 containing the bupropion base 16 or combination of bupropion base and nicotine, nicotine metabolite, nicotine and a nicotine metabolite or an azapirone either dispersed therein, or adsorbed or absorbed by a particulate hydrophilic material, and a release liner 18.

Reservoir layer 14 in FIG. 1 is a means for containing the bupropion base 16 or combination of bupropion base and nicotine, nicotine metabolite, nicotine and a nicotine metabolite or an azapirone and an adhesive for securing the patch 10 to the skin during use. As release liner 18 is removed prior to the application of the patch to the skin, reservoir layer 14 serves as the basal surface of the patch which adheres to the skin. Reservoir layer 14 includes a pressure-sensitive adhesive suitable for long term skin contact. Reservoir layer 14 is physically and chemically compatible with bupropion base, and nicotine, nicotine metabolite, nicotine and a nicotine metabolite or an azapirone, and the carriers and vehicles employed.

Figure 2:
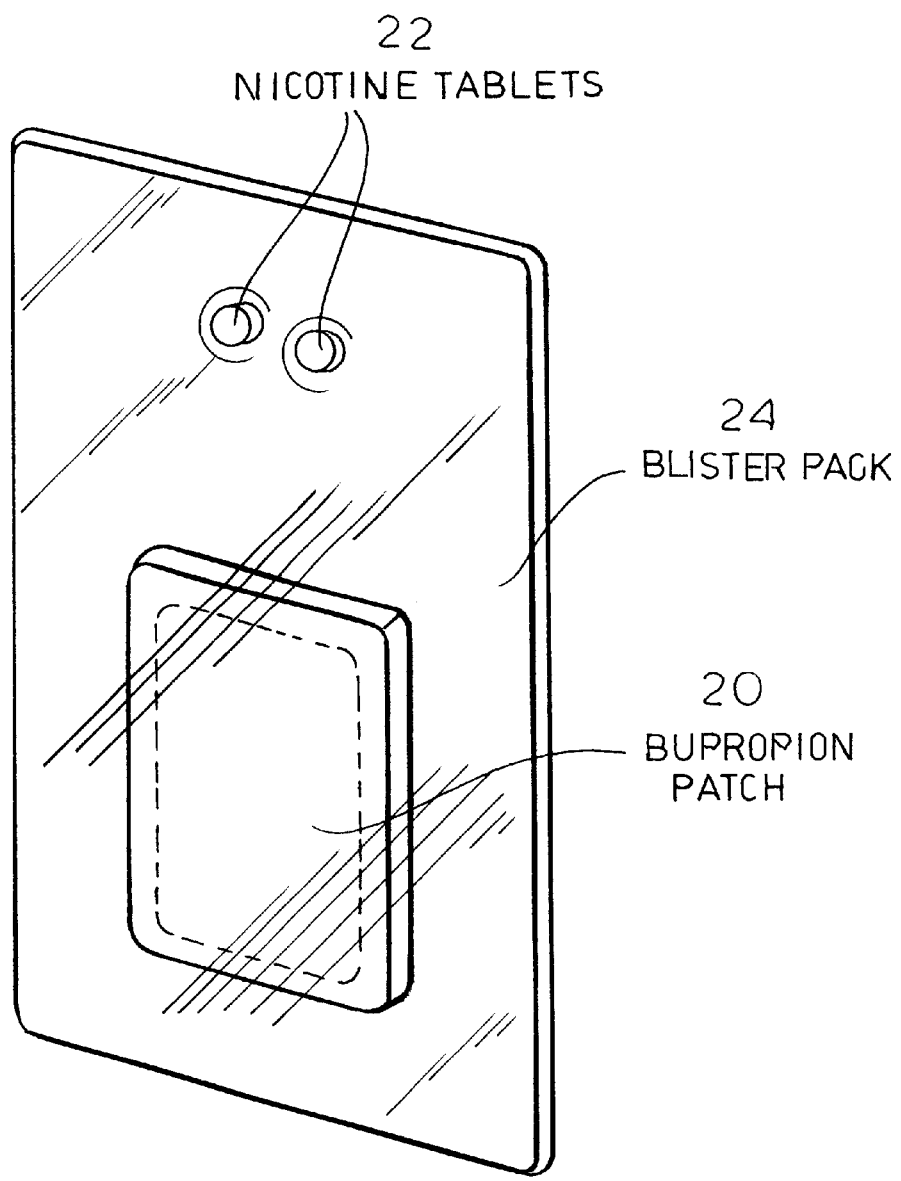
FIG. 2 is a schematic illustration of a kit that comprises the transdermal delivery system containing the bupropion patch and a series of nicotine tablets surrounded by a packaging material.

The embodiment in FIG. 2 includes a transdermal delivery system containing a patch containing stabilized bupropion base 20, a series of nicotine tablets 22, and a blister pack 24 surrounding the patch and the tablets.

EXAMPLES

Example 1

The unit contains all the necessary nicotine gum and bupropion patches for an eight-week treatment.

The phased treatment is divided into 4 colors coded segments:

| Week 1 | blue |
|---|---|
| Week 2 | red |
| Week 3–6 | green |
| Week 7–8 | white |

To further aid the patient. The package is divided in layers- each layer is separated by a physical barrier, e.g. paper.

The nicotine gum tablets in layers 2 (red) 4 (white) will be packaged on a card which differentiates them "one tablet every two hours" red and the next layer will have the carded nicotine tablets in green "one tablet every two hours".

The last segment will be color coded white and the carded tablets will be color-coded and designated "one tablet every 4 hours".

The therapy described below is for an individual smoking more than 25 cigarettes/day/under this number of cigarettes-substitute 2 mg gum.

Week 1

The patient continues smoking for the first week that the bupropion patch is used. The patch contains an equivalent amount of 75 mg bupropion. The patch is applied daily for the first 3 days. The patch is removed prior to sleeping and reapplied when the patient awakes.

After the 3rd day a patch containing the equivalent of 150 mg of bupropion is applied. The 150 mg patch is worn during the waking hours and is removed prior to sleep and is reapplied upon awaking for 4 days. The bupropion alleviates the anxiety and depression associated with commencing a nicotine withdrawal cessation program. It takes a week to reach the appropriate bupropion plasma levels.

Week 2 (The Patient Stops Smoking)

4 mg (1 q 2 hrs.—no more than 12 pieces of nicotine gum tablets) 84 nicotine gum pieces+7 bupropion patches Week 3–6 same regime Week 7–8

4 mg 1 q 4 h—no more than 4 pieces of nicotine gum–28 nicotine gum pieces+7 bupropion patches (weeks supply)

2 week supply=56 pieces of nicotine gum and 14 bupropion patches

Example 2

A unit similar to the one employed in Example 1 is employed here except that in place of the nicotine gum, a patch containing nicotine is provided for transdermal administration of nicotine.

Example 3

A unit similar to the one employed in Example 1 is employed here except that in place of the nicotine gum, a nasal spray inhaler containing nicotine is provided for intra-nasal administration of nicotine.

Example 4

A unit similar to the one employed in Example 1 is employed here except that in place of the bupropion patch and the nicotine gum, a patch which contains bupropion and either nicotine, an active nicotine metabolite or a combination of active nicotine metabolites or pharmaceutically acceptable salts thereof is provided.

What is claimed is:

1. A pharmaceutical composition in unit dosage form to alleviate tobacco-smoking withdrawal symptoms which consists essentially of:
   (a) a therapeutically effective amount of nicotine, at least one active nicotine metabolite, a combination of nicotine and an active nicotine metabolite, or an azapirone, or a pharmaceutically acceptable salt thereof; and
   (b) a transdermal delivery system comprising bupropion base in a therapeutically effective amount.

2. The pharmaceutical composition defined in claim 1 wherein the transdermal delivery system is a patch for transdermal delivery of bupropion to a mammalian subject, said patch comprising:
   (i) a flexible, inert backing layer incapable of absorbing bupropion base;
   (ii) a release liner through which bupropion base is not permeable; and
   (iii) a reservoir located between the backing layer and the release liner, said reservoir having a bupropion-transfer surface adjacent to the release liner and adapted to contact the skin of the patient and sufficient to transfer an effective dosage of bupropion base through the skin of said patient into the bloodstream of said patient, which comprises:
      (1) a therapeutically effective amount of bupropion base selected from the group which consists of (+)-bupropion base, (−)-bupropion base and racemic bupropion base and mixtures thereof; and
      (2) means for securing the bupropion-transfer surface area of said reservoir to the skin of the patient.

3. The pharmaceutical composition defined in claim 2 wherein the reservoir containing bupropion base includes a stabilizer to effectively stabilize the bupropion base.

4. The pharmaceutical composition defined in claim 3 wherein the stabilizer is selected from the group consisting of L-ascorbic acid palmitate, tocopherol solution in alcohol, butylated hydroxyanisole, vitamin E succinate, Vitamin E 700 acetate, and L-ascorbic acid G palmitate, and is present in the reservoir containing the bupropion base in an amount of 2.7 to 27% by weight of the bupropion base.

5. The pharmaceutical composition defined in claim 1 wherein the nicotine, at least one active nicotine metabolite, a combination of nicotine and an active nicotine metabolite, or an azapirone, or a pharmaceutically acceptable salt thereof is in an oral dose as a tablet or capsule.

6. The pharmaceutical composition defined in claim 1 wherein the unit dosage form containing the nicotine, at least one active nicotine metabolite, a combination of nicotine and an active nicotine metabolite, or an azapirone, or a pharmaceutically acceptable salt thereof is contained in a patch for transdermal delivery.

7. The pharmaceutical composition defined in claim 1 wherein the azapirone is selected from the group consisting of buspirone, gepirone, ipsapirone, tandospirone, WY-47,846, MDL-73005 EF, and BP-554.

8. The pharmaceutical composition defined in claim 1 wherein the nicotine, at least one active nicotine metabolite, a combination of nicotine and an active nicotine metabolite, or an azapirone, or a pharmaceutically acceptable salt thereof is in a chewing gum.

9. The pharmaceutical composition defined in claim 1 wherein the nicotine, at least one active nicotine metabolite, a combination of nicotine and an active nicotine metabolite, or an azapirone, or a pharmaceutically acceptable salt thereof is in a nasal spray inhaler or nasal vapor inhaler.

10. The pharmaceutical composition defined in claim 1 wherein the nicotine, at least one active nicotine metabolite, a combination of nicotine and an active nicotine metabolite, or an azapirone, or a pharmaceutically acceptable salt thereof is in an aqueous solution.

11. The pharmaceutical composition defined in claim 2 wherein the nicotine, at least one active nicotine metabolite, a combination of nicotine and an active nicotine metabolite, or an azapirone, or a pharmaceutically acceptable salt thereof is included within the reservoir containing the bupropion base in the transdermal patch.

12. The pharmaceutical composition defined in claim 1 wherein the therapeutically effective amount of the nicotine, at least one active nicotine metabolite, a combination of nicotine and an active nicotine metabolite, or an azapirone, or a pharmaceutically acceptable salt thereof is in a tablet suitable for intraoral administration or is in a tablet suitable for oral administration.

13. The pharmaceutical composition defined in claim 1 wherein the therapeutically effective amount of the nicotine, at least one active nicotine metabolite, a combination of nicotine and an active nicotine metabolite, or an azapirone, or a pharmaceutically acceptable salt thereof is in a capsule suitable for intraoral administration or is in a capsule suitable for oral administration.

14. The pharmaceutical composition defined in claim 1 wherein the therapeutically effective amount of the nicotine, at least one active nicotine metabolite, a combination of nicotine and an active nicotine metabolite, or an azapirone, or a pharmaceutically acceptable salt thereof is in a lozenge suitable for intraoral administration.

15. A method of alleviating tobacco-smoking withdrawal symptoms in a patient who is refraining from smoking tobacco which comprises the step of administering to said patient a therapeutically effective amount of a pharmaceutical composition in unit dosage form to alleviate tobacco-smoking withdrawal symptoms which consists essentially of:
   (a) a therapeutically effective amount of nicotine, at least one active nicotine metabolite, a combination of nicotine and an active nicotine metabolite, or an azapirone, or a pharmaceutically acceptable salt thereof; and
   (b) a transdermal delivery system comprising bupropion base in a therapeutically effective amount.

16. The method of alleviating tobacco-smoking withdrawal symptoms in a patient who is refraining from smoking tobacco defined in claim 15 wherein the therapeutically effective amount of the nicotine, at least one active nicotine metabolite, a combination of nicotine and an active nicotine metabolite, or an azapirone, or a pharmaceutically acceptable salt thereof ranges from 1 to 100 mg/kg of body weight of the patient and wherein the therapeutically effective amount of transdermally administered bupropion base selected from the group which consists of (+)-bupropion base, (−)-bupropion base and racemic bupropion base and mixtures thereof ranges between 40 and 300 mg/day.

17. The method of alleviating tobacco-smoking withdrawal symptoms in a patient who is refraining from smoking tobacco defined in claim 15, wherein the therapeutically effective amount of the nicotine, at least one active nicotine metabolite, a combination of nicotine and an active nicotine metabolite, or an azapirone, or a pharmaceutically acceptable salt thereof is administered intraorally or orally.

18. The method of alleviating tobacco-smoking withdrawal symptoms in a patient who is refraining from smoking tobacco defined in claim 15 wherein the therapeutically effective amount of the nicotine, at least one active nicotine metabolite, a combination of nicotine and an active nicotine metabolite, or an azapirone, or a pharmaceutically acceptable salt thereof is administered transdermally.

19. The method of alleviating tobacco-smoking withdrawal symptoms in a patient who is refraining from smoking tobacco defined in claim 15 wherein the therapeutically effective amount of the nicotine, at least one active nicotine metabolite, a combination of nicotine and an active nicotine metabolite, or an azapirone, or a pharmaceutically acceptable salt thereof is administered intranasally.

20. A kit to alleviate tobacco-smoking withdrawal symptoms in a patient which consists essentially of:
(a) a therapeutically effective amount of nicotine, at least one active nicotine metabolite, a combination of nicotine and an active nicotine metabolite, or an azapirone, or a pharmaceutically acceptable salt thereof;
(b) a transdermal delivery system comprising bupropion base in a therapeutically effective amount; and
(c) a packaging material surrounding (a) and (b).

21. The kit defined in claim 20 wherein the packaging material is a box, bottle, tube, sprayer, insufflator or envelope.

22. The kit defined in claim 20 wherein the transdermal delivery system is a patch for transdermal delivery of bupropion to a mammalian subject, said patch comprising:
(i) a flexible, inert backing layer incapable of absorbing bupropion base;
(ii) a release liner through which bupropion base is not permeable; and
(iii) a reservoir located between the backing layer and the release liner, said reservoir having a bupropion-transfer surface adjacent to the release liner and adapted to contact the skin of the patient and sufficient to transfer an effective dosage of bupropion base through the skin of said patient into the bloodstream of said patient, which comprises:
(1) a therapeutically effective amount of bupropion base selected from the group which consists of (+)-bupropion base, (−)-bupropion base and racemic bupropion base and mixtures thereof; and
(2) means for securing the bupropion-transfer surface area of said reservoir to the skin of the patient.

* * * * *